United States Patent [19]

Soma

[11] 4,375,480
[45] Mar. 1, 1983

[54] FACIAL SKIN ACTIVATOR EMULSION AND METHOD OF SKIN MOISTURIZING AND CLEANSING

[76] Inventor: William D. Soma, 17436 Tarzana St., Encino, Calif. 91316

[21] Appl. No.: 275,633

[22] Filed: Jun. 22, 1981

[51] Int. Cl.$^3$ .............................................. A61K 47/00
[52] U.S. Cl. .................................... 424/358; 424/365
[58] Field of Search ............................... 424/358, 365

[56] References Cited

U.S. PATENT DOCUMENTS

| | | | |
|---|---|---|---|
| 4,143,160 | 3/1979 | Osberghaus | 424/365 |
| 4,254,104 | 3/1981 | Suzuki | 424/365 |
| 4,254,105 | 3/1981 | Fukuda | 424/365 |
| 4,264,581 | 4/1981 | Kerkhof | 424/365 |
| 4,268,502 | 5/1981 | Martin | 424/365 |
| 4,272,544 | 6/1981 | Cella et al. | 424/358 |
| 4,278,570 | 7/1981 | Flom et al. | 424/365 |

OTHER PUBLICATIONS

Ash et al, A Formulary of Cosmetic Preparations, 1977, pp. 273-276,277,287,301,302,303.
Harry, The Principles and Practice of Modern Cosmetics, 1963, pp.49-56.

*Primary Examiner*—Dale R. Ore
*Attorney, Agent, or Firm*—John J. Posta, Jr.

[57] ABSTRACT

An improved hypoallergenic facial skin activator emulsion and method of moisturizing and cleansing skin are provided. The emulsion has, by weight, about 50-80 parts water, about 8-35 parts of unsaturated vegetable oil, preferably sesame oil, about 5-10 parts of humectant comprising glycerin, about 0.5-1 part of Triethanolamine, about 0.1-0.5 parts of cetyl alcohol, about 0.8-3 parts of lanolin oil, about 0.1-0.5 parts of an emulsifier selected from the group consisting of the monopalmitate, monooleate or monostearate of polyoxyethylene sorbitan, and mixtures thereof, and about 2.5-4 parts of an emulsifier selected from the group consisting of sorbitan palmitate, sorbitan oleate, sorbitan stearate and mixtures thereof. The emulsion may also include a preservative comprising methyl paraben, propyl paraben or both, a thickening agent such as glyceryl monostearate, and artificial or natural color and fragrance, as well as vitamin E or the like as an antioxidant. The method comprises massaging a quantity of the emulsion completely into the facial skin, then flooding the skin with water until the water penetrates into the skin via the emulsion and moisturizes and cleanses the skin. The emulsion absorbs some of the water and also provides softening agents for the skin. The emulsion is inexpensive and highly effective for preserving and renewing the vitality of the skin.

2 Claims, No Drawings

FACIAL SKIN ACTIVATOR EMULSION AND METHOD OF SKIN MOISTURIZING AND CLEANSING

BACKGROUND OF THE INVENTION

1. Field of the Invention

The present inventor generally relates to emulsions and more particularly to an improved hypoallergenic emulsion for use in revitalizing human skin.

2. Prior Art

Various types of skin care products are on the market. Certain cremes are used to cleanse the human skin and others to moisturize it. However, few are capable of having any substantial and lasting effect on human skin, particularly within and below the epidermis. Most of those cremes that do produce significant results are very expensive. Certain of such cremes are allergenic to sensitive individuals and cannot be used without adverse skin reactions.

Inasmuch as cosmetic appearance is and should be important to all, young and old alike, there is a need for an improved skin care formulation which will preferably be hypoallergenic and will produce long-lasting deep penetration, cleansing and moisturizing of human skin and which is relatively inexpensive and easy to use. Such a preparation should be capable of protecting the skin against dehydration and wrinkling and also be capable of removing deep seated dirt and debris from the skin, all through the use of a simple method of application.

SUMMARY OF THE INVENTION

The improved skin care formulation and method of use of the present invention satisfy all the foregoing needs. The formulation and method are substantially as set forth in the Abstract above. Thus, the formulation is a hypoallergenic emulsion comprising a major proportion of water and substantial proportions of unsaturated vegetable oil, most preferably sesame oil, lanolin oil and glycerin. Softening agent such as Triethanolamine and cetyl alcohol and selected emulsifiers such as polyoxyethylene sorbitan monostearate and sorbitan oleate are also present in minor amounts. Preferably, bacteriostats such as methyl paraben and propyl paraben and a thickening agent such as glyceryl monostearate are also in the formulation. The proportions of ingredients in the formulation as set forth in the Abstract above are necessary to provide the desired results.

In using the emulsion, it is first spread over the skin, such as facial skin, and then massaged completely into the skin. The massaging has the effect of softening and smoothing the skin and stimulating the sweat glands so as to dislodge and remove dirt from the skin. Brown pigmentation spots on the skin surface tend to disappear. The skin is then flooded with water until the water is absorbed via the emulsion into the skin, moisturizing the skin, further softening it and rendering it supple and healthy. The water also cleanses the skin and thus the skin is revitalized and protected against wrinkling. The emulsion which has penetrated and lies within the skin tends to retain water in the absorbed state in the skin for long lasting results. Further features of the invention are set forth in the following detailed description.

DETAILED DESCRIPTION OF THE PREFERRED EMBODIMENT

The improved emulsion formulation of the present invention comprises the essential ingredients and their essential concentration ranges, as set forth in Table I below:

TABLE I

| | Ingredients | Concentration (parts by weight) |
|---|---|---|
| (a) | water | about 50–80 |
| (b) | glycerin | about 5–10 |
| (c) | unsaturated vegetable oil | about 8–35 |
| (d) | lanolin oil | about 0.8–3 |
| (e) | emulsifier (A) selected from the group consisting of sorbitan palmitate, sorbitan oleate, sorbitan stearate and mixtures thereof | about 2.5–4 |
| (f) | Triethanolamine | about 0.5–1 |
| (g) | cetyl alcohol | about 0.1–0.5 |
| (h) | emulsifier (B) selected from the monopalmitate, monooleate and monostearate of polyoxyethylene sorbitan and mixtures thereof | about 0.1–0.5 |

Of the above ingredients, it is much preferred to use sesame oil for the vegetable oil, since it provides enhanced results. Thus, it speeds penetration and softening of the skin, and performs in a superior manner as the main emollient and moisturizer in the formulation. The exact mechanism for its improved results is not known. Sesame oil is a blond liquid oil with a melting point of about 20°–25° C. It comprises about 75 percent olein (the Triglyoride of oleic acid) as well as smaller concentrations of stearin, palmitin, myristin, linolein, sesamin and sesamolin. Stearin, palmitin, myristin and linolein are the triglycerides of, respectively, the saturated fatty acids stearic acid, palmitic acid and myristic acid, and the unsaturated fatty acid linoleic acid. Sesamin is 2,6-bis[3,4-(methylene dioxy)phenyl]-3,7-di-oxabicyclo[3.3.0]octane, while sesamolin is 6-[3,4-(methylenedioxy)phenoxy]-2-[3,4-(methylenedioxy)-phenyl]-3,7-dioxabicyclo[3.3.0]octane. Sesame oil is particularly compatible with human skin, is hypoallergenic and is easily absorbed in the skin.

It will be understood that instead of sesame oil, another highly unsaturated vegetable oil having the required properties of compatibility with the human skin, hypoallergenicity and the ability to function as a superior emollient and moisturizer could be used, in whole or in part; for example, olive oil, peanut oil, cottonseed oil and the like. Of such oils, those most similar to sesame oil in fatty acid glyceride constituents and concentrations are best. However, sesame oil is the vegetable oil of choice in the emulsion.

In the formulation of Table I, glycerin, which is 1,2,3-propanetriol, serves as an humectant and skin softener. Lanolin oil, derived from wool fat, and composed of cholesterol esters of fatty acids, is an emollient and moisturizer, which aids and supports the action of the sesame oil being readily absorbed into the skin. Cetylalcohol which is 1-hexadecanol, has a plural function, serving as a moisturizer and viscosity builder, but also skin softener and emulsifier. Triethanolamine, which is Tri(2-hydroxyethyl)amine, also serves as an emulsifier, skin softening agent and humectant in the formulation. The other constituents, except water, listed in Table I are emulsifiers to facilitate the formation of the all-in-water emulsion which comprises the novel formulation.

The preferred range of concentrations of the necessary ingredients specified in Table I is set forth in Table II below. This range is capable of providing optimal results.

TABLE II

|   | Ingredients | Concentration (parts by weight) |
|---|---|---|
| (a) | water | 51.5–77.1 |
| (b) | glycerin | 6.5–8.5 |
| (c) | unsaturated vegetable oil (preferably sesame oil) | 10–30 |
| (d) | lanolin oil | 0.9–2.5 |
| (e) | emulsifier A (see Table I) | 2.75–3.75 |
| (f) | Triethanolamine | 0.5–1.0 |
| (g) | cetyl alcohol | 0.1–0.5 |
| (h) | emulsifier B (see Table I) | 0.1–0.5 |

In addition, certain other ingredients are preferably present in the improved formulation of the present invention. These include glyceryl monostearate, a thickening agent and emulsifier, in about 1.5 parts concentration as well as the preservatives methylparaben (about 0.15 parts) and propyl paraben (about 0.1 parts). Color, and fragrance artificial or natural, may also be added in small concentrations for example, about 0.1–0.2 parts each. Yellow #6FD and C and Red #40 FD and C can, for example, be used. Imidazolidinyl urea can be used in, for example, 0.2 parts amount, as an antioxidant. Vitamin E is preferred for use, for example in an amount of about 0–1 part, as a skin nutrient and an antioxidant for the unsaturated vegetable oil to prevent rancidity. Vitamins A and D can be added in, for example, an amount of about 0–2 parts, as skin nutrients.

The following specific Examples illustrate certain further features of the present invention.

EXAMPLE I

An improved facial skin activator formulation in accordance with the present invention is prepared, utilizing the ingredients and concentrations set forth in Table III below:

TABLE III

| Ingredients | Concentrations |
|---|---|
| deionized water | 60.25 gals. |
| glycerin | 60 lbs. |
| Triethanolamine | 5 lbs. 6 ozs. |
| polyoxyethylene sorbitan monostearate | 1 lb. 10 ozs. |
| methyl paraben | 1 lb. 4 ozs. |
| lanolin oil | 12 lbs. |
| cetyl alcohol | 3 lbs. |
| sesame oil (USP grade) | 172 lbs. |
| sorbitan monostearate | 26 lbs. |
| glyceryl monostearate, self-emulsifying | 12 lbs. |
| Vitamin E | 181 grams |
| propyl paraben | 362 grams |
| Imidazolidinyl urea | 1 lb. 10 ozs. |
| Vitamins A and D | 362 grams |

TABLE III-continued

| Ingredients | Concentrations |
|---|---|
| Yellow #6 FD and C (conc. of 2 oz/gal) | 58 mls. |
| Red #40 FD and C (conc. of 2 oz/gal) | 29 mls. |
| Fragrance (Flower essence) | 1 lb. 4 ozs. |
| Make-up water | To bring to 96 gal total for formulation (800 lbs.) |

In preparing the formulation of Table II, the deionized water is passed into a 200 gallon steam jacketed kettle fitted with a motorized stirrer, and the glycerin, Triethanolamine, polyoxyethylene sorbitan monostearate and methyl paraben are added thereto. This stirred first mixture is heated in the kettle to 70° C. Meanwhile, the lanolin oil, vitamin E and propylparaben cetyl alcohol, sesame oil, sorbitan monostearate, glyceryl monostearate, are mixed together by a mechanical stirrer in a separate similar steam jacketed kettle while being heated to 70° C. to provide a liquid second mixture. After about 20 minutes of heating and stirring, the second mixture is added to the first mixture with stirring until an emulsion is formed, whereupon the emulsion is stirred and cooled to 40° C. The remaining ingredients are then slowly added to the emulsion, with stirring, the last one added being the make-up water to bring the total volume to 96 gals. (800 lbs.). The product is then ready for use.

When a small amount (approximately ¼ oz.) of the formulation of Table III, prepared as described above, is completely massaged into the human facial skin each day over a period of, for example, 1–3 minutes, and then the face is flooded with water for, for example 2–3 minutes, and thereafter patted dry, revitalization of the treated skin occurs, with improvement of skin texture, color and clarity being noticeable within a week. Such a daily procedure maintains the health, clean condition, elasticity and vitality of the skin, reducing or eliminating blemishes, brown spots and the like and freeing dirt and grime from the skin, stimulating the sebaceous glands and toning the skin. The formulation, as previously noted, absorbs water, aids its penetration into the skin and helps to retain it in the skin so as to moisturize it and keep it moist. The humectants in the formulation aid in this process. The formulation softens, soothes, smooths and stimulates the skin and combines with the massaging to facilitate proper circulation with and nutrition of the skin. Moreover, the formulation is inexpensive to manufacture and easy to use, little of the formulation being needed daily to produce the desired results.

EXAMPLE II

Two batches, A and B, of the improved formulation of the present invention are prepared in the manner set forth in Example I but have the compositions set forth in Table IV below.

TABLE IV

| Ingredients | Parts by weight (Batch A) | Parts by weight (Batch B) |
|---|---|---|
| deionized water | 51.5 | 77.1 |
| glycerin | 8.5 | 6.8 |
| Triethanolamine | 1.0 | 0.5 |
| polyoxyethylene sorbitan monostearate | 1.0 | 0.5 |
| methyl paraben | 0.15 | 0.15 |

TABLE IV-continued

| Ingredients | Parts by weight (Batch A) | Parts by weight (Batch B) |
| --- | --- | --- |
| lanolin oil | 2.5 | 0.9 |
| cetyl alcohol | 0.5 | 0.1 |
| sesame oil | 30 | 10 |
| sorbitan stearate | 3.75 | 2.75 |
| glyceryl monostearate | 1.5 | 1.5 |
| propyl paraben | 0.1 | 0.1 |
| color (red and yellow) | 0.1 | 0.1 |
| fragrance | 0.2 | 0.2 |
| Vitamin E | 0.1 | 0.2 |

Both formulations (batch A and B) have properties similar to those of the formulation of Example I when used on a daily basis on human facial skin in the manner described in Example I. Thus, they effectively clean and moisturize, tone and activate the skin, stimulating its health and vitality. Formulations utilizing the same ingredients but in concentrations substantially outside the required ranges of concentrations specified above do not provide comparable results to the formulations of the present invention when applied to the skin. Accordingly, the advantages and benefits of the present formulation and method are clear. Other features of the present invention areas set forth in the foregoing.

Various modifications, changes, alterations and additions can be made in the formulation of the present invention, its ingredients and their parameters and in the improved method of the present invention, its steps and their parameters. All such modifications, changes, alterations and additions as are within the scope of the appended claims form part of the present invention.

What is claimed is:

1. An improved method of treating human skin to moisturize and cleanse it, said method comprising:
   (a) applying to and massaging completely into human skin an emulsion having the following essential composition:

| Ingredients | Parts by weight |
| --- | --- |
| water | 50–80 |
| glycerin | 5–10 |
| Triethanolamine | 0.5–1 |
| emulsifier selected from the group consisting of polyoxyethylene sorbitan monopalmitate, polyoxyethylene sorbitan monoleate, polyoxyethylene sorbitan monostearate and mixtures | 0.1–0.5 |
| unsaturated vegetable oil | 8–35 |
| cetyl alcohol | 0.1–0.5 |
| lanolin oil | 0.8–3 |
| emulsifier selected from the group consisting of sorbitan palmitate, sorbitan oleate; sorbitan stearate and mixtures thereof | 2.5–4 |

(b) flooding said skin with water and,
   (c) maintaining said flooding until said water penetrates into and moisturizes and cleanses said skin, said emulsion absorbing said water and aiding said moisturizing.

2. The improved method of claim 1 wherein said skin comprises facial skin and said emulsion has the following approximate composition:

| Ingredients | Parts by weight |
| --- | --- |
| deionized water | 51.5–77.1 |
| glycerin | 6.8–8.5 |
| polyoxyethylene sorbitan monostearate | 0.5–1.0 |
| Triethanolamine | 0.5–1.0 |
| methyl paraben | 0.15 |
| lanolin oil | 0.9–2.5 |
| cetyl alcohol | 0.1–0.5 |
| sesame oil | 10–30 |
| sorbitan stearate | 2.75–3.75 |
| glyceryl monostearate | 1.5 |
| propyl paraben | 0.1 |
| color | 0.05 |
| fragrance | 0.05 |

* * * * *